US00PP34084P2

(12) United States Plant Patent
Arts

(10) Patent No.: US PP34,084 P2
(45) Date of Patent: Apr. 5, 2022

(54) BLUEBERRY PLANT NAMED 'FV1907'

(50) Latin Name: *Vaccinium corymbosum*
Varietal Denomination: FV1907

(71) Applicant: FV B.V., De Kwakel (NL)

(72) Inventor: Niels Arts, Aalsmeer (NL)

(73) Assignee: FV B.V., De Kwakel (NL)

( * ) Notice: Subject to any disclaimer, the term of this patent is extended or adjusted under 35 U.S.C. 154(b) by 0 days.

(21) Appl. No.: 17/357,863

(22) Filed: Jun. 24, 2021

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368
See application file for complete search history.

(56) References Cited

PUBLICATIONS

UPOV hit on a blueberry plant named, 'FV1907', QZ PBR 2020/0965, fled Apr. 6, 2020.*
CPVO hit on a blueberry plant named, 'FV19071'. https://cpvo.europa.eu/en/applications-and-examinations/official-publications accessed Sep. 10, 2021.*

* cited by examiner

*Primary Examiner* — Anne Marie Grunberg
(74) *Attorney, Agent, or Firm* — C. Anne Whealy

(57) ABSTRACT

A new and distinct cultivar of Blueberry plant named 'FV1907', characterized by its semi-upright and bushy plant habit; vigorous growth habit; freely branching habit; early fruiting with relatively low chilling requirement; high fruit yield; large dark blue-colored spherical fruits; sweet fruit taste; and good fruit postharvest longevity.

2 Drawing Sheets

Figure 1:
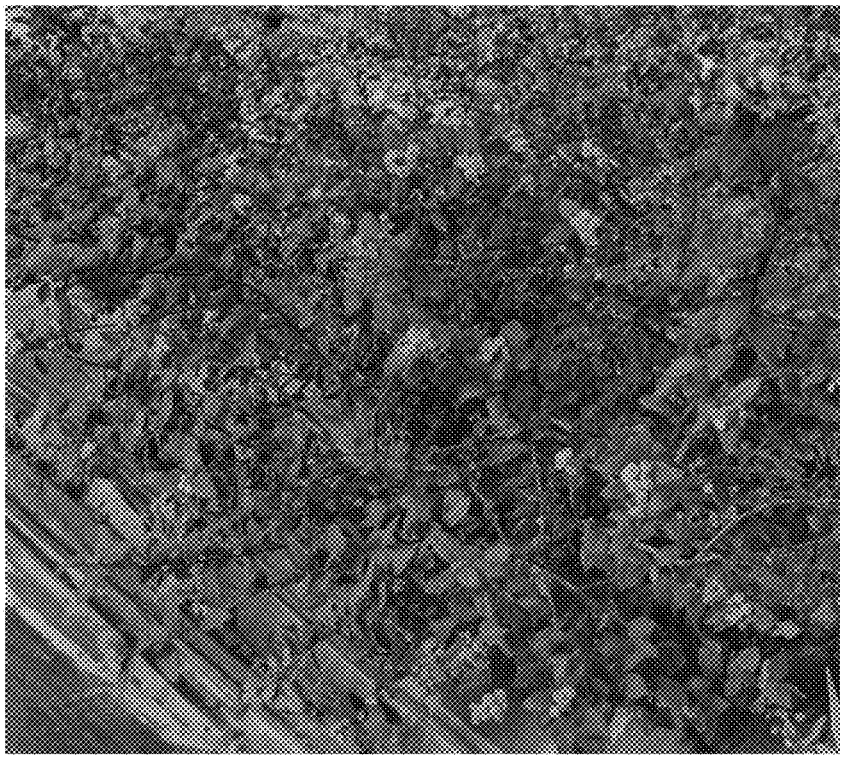

Botanical designation: *Vaccinium corymbosum.*
Cultivar denomination: 'FV1907'.

CROSS-REFERENCED TO CLOSELY-RELATED APPLICATIONS

Title: Blueberry Plant Named 'FV1904'
Inventor: Niels Arts
Filed: Concurrently with the instant application having application Ser. No. 17/357,809
Title: Blueberry Plant Named 'FV1906'
Inventor: Niels Arts
Filed: Concurrently with the instant application having application Ser. No. 17/357,842
Title: Blueberry Plant Named 'FV1908'
Inventor: Niels Arts
Filed: Concurrently with the instant application having application Ser. No. 17/357,871

STATEMENT REGARDING PRIOR DISCLOSURES BY INVENTOR & APPLICANT/ASSIGNEE

An European Community Plant Breeder's Rights application for the instant plant was filed by the Applicant/Assignee, FV B.V. of De Kwakel, The Netherlands on Apr. 6, 2020, application number 2020/0965. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present Invention relates to a new and distinct cultivar of Blueberry plant, commonly referred to as Highbush Blueberry, botanically known as *Vaccinium corymbosum* and hereinafter referred to by the name 'FV1907'.

The new Blueberry plant is a product of a planned breeding program conducted by the Inventor in De Kwakel, The Netherlands and Lepe, Spain. The objective of the breeding program was to develop new early-fruiting Blueberry plants with large fruits and good fruit quality, productivity, uniformity and postproduction longevity.

The new Blueberry plant originated from a cross-pollination in 2014 in De Kwakel, The Netherlands by the Inventor of *Vaccinium corymbosum* 'Emerald', disclosed in U.S. Plant Pat. No. 12,165, as the female, or seed, parent with *Vaccinium corymbosum* 'Snowchaser' disclosed in U.S. Plant Pat. No. 19,503, as the male, or pollen, parent. The new Blueberry plant was discovered and selected by the Inventor as a single plant from within the progeny of the stated cross-pollination in a controlled environment in Lepe, Spain in February, 2017.

Asexual reproduction of the new Blueberry plant by stem cuttings in a controlled environment at Lepe, Spain since June, 2017 has shown that the unique features of this new Blueberry plant are stable and reproduced true to type in successive generations of asexual reproduction.

SUMMARY OF THE INVENTION

Plants of the new Blueberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'FV1907'. These characteristics in combination distinguish 'FV1907' as a new and distinct Blueberry plant:

1. Semi-upright and bushy plant habit.
2. Vigorous growth habit.
3. Freely branching habit.
4. Early fruiting with relatively low chilling requirement.
5. High fruit yield.
6. Large dark blue-colored spherical fruits.
7. Sweet fruit taste.
8. Good fruit postharvest longevity.

Plants of the new Blueberry differ primarily from plants of the female parent, 'Emerald', in the following characteristics:

1. Plants of the new Blueberry produce fruit about two months earlier than plants of 'Emerald'.
2. Fruits of plants of the new Blueberry are firmer than fruits of plants of 'Emerald'.
3. Plants of the new Blueberry have a 100 hour chilling requirement whereas plants of 'Emerald' have a 250 hour chilling requirement.

Plants of the new Blueberry differ primarily from plants of the male parent, 'Snowchaser', in the following characteristics:

1. Plants of the new Blueberry are not as upright as plants of 'Snowchaser'.
2. Plants of the new Blueberry produce larger fruit than plants of 'Snowchaser'.

Plants of the new Blueberry can be compared to plants of *Vaccinium corymbosum* 'FV1904', disclosed in U.S. Plant Patent application filed concurrently having application Ser. No. 17/357,809. In side-by-side comparisons, plants of the new Blueberry differ from plants of 'FV1904' in the following characteristics:

1. Plants of the new Blueberry are not as upright as plants of 'FV1904'.
2. Plants of the new Blueberry have a 100 hour chilling requirement whereas plants of 'FV1904' have a 150 hour chilling requirement.
3. Plants of the new Blueberry produce slightly larger fruits than plants of 'FV1904'.
4. Plants of the new Blueberry produce less fruit per plant than plants of 'FV1904'.

Plants of the new Blueberry can be compared to plants of *Vaccinium corymbosum* 'FV1906', disclosed in U.S. Plant Patent application filed concurrently having application Ser. No. 17/357,842. In side-by-side comparisons, plants of the new Blueberry differ from plants of 'FV1906' in the following characteristics:

1. Plants of the new Blueberry are not as upright as plants of 'FV1906'.
2. Plants of the new Blueberry have a 100 hour chilling requirement whereas plants of 'FV1906' have a 150 hour chilling requirement.
3. Fruits of plants of the new Blueberry are not as firm as fruits of plants of 'FV1906'.
4. Fruits of plants of the new Blueberry are sweeter than fruits of plants of 'FV1906'.

Plants of the new Blueberry can be compared to plants of *Vaccinium corymbosum* 'FV1908', disclosed in U.S. Plant Patent application filed concurrently having application Ser. No. 17/357,871. In side-by-side comparisons, plants of the new Blueberry differ from plants of 'FV1908' in the following characteristics:

1. Plants of the new Blueberry are not as upright as plants of 'FV1908'.
2. Fruits of plants of the new Blueberry are sweeter than fruits of plants of 'FV1908'.

Plants of the new Blueberry can also be compared to plants of *Vaccinium corymbosum* 'Star', disclosed in U.S. Plant Pat. No. 10,675. In side-by-side comparisons, plants of the new Blueberry differ from plants of 'Star' in the following characteristics:

1. Plants of the new Blueberry are not as upright as plants of 'Star'.
2. Plants of the new Blueberry are more vigorous and broader than plants of 'Star'.
3. Plants of the new Blueberry have a 100 hour chilling requirement whereas plants of 'Star' have a 400 hour chilling requirement.
4. Plants of the new Blueberry produce fruit about four months earlier than plants of 'Star'.
5. Plants of the new Blueberry produce larger fruit than plants of 'Star'.

BRIEF DESCRIPTION OF THE PHOTOGRAPHS

The accompanying colored photographs illustrate the appearance of the new Blueberry plant showing the colors as true as it is reasonably possible to obtain in colored reproductions of this type. Colors in the photographs may differ slightly from the color values cited in the detailed botanical description which accurately describe the colors of the new Blueberry plant.

The photograph on the first sheet (FIG. 1) is a side perspective view of typical flowering and fruiting plants of 'FV1907'.

Figure 2:
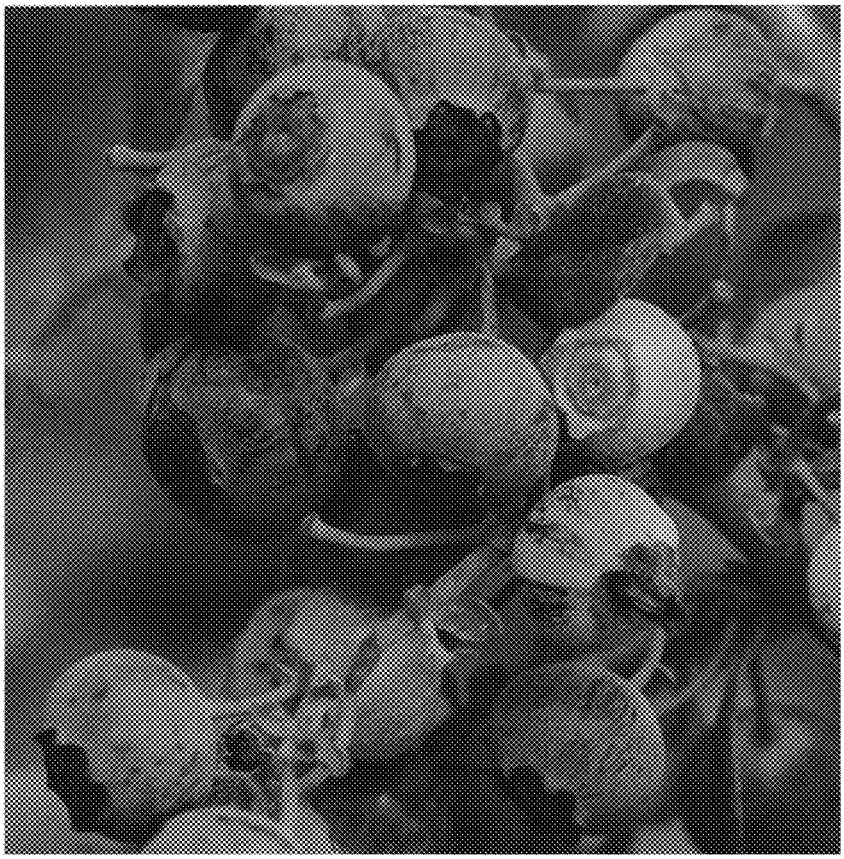

The photograph on the second sheet (FIG. 2) is a close-up view of typical developing and developed fruits of 'FV1907'.

DETAILED BOTANICAL DESCRIPTION

The aforementioned photographs, following observations and measurements describe plants grown during the spring, summer and autumn in ground beds in a polyethylene-covered greenhouse in Lepe, Spain and under typical cultural practices of Blueberry plant production. During the production of the plants, day temperatures averaged 26° C. and night temperatures averaged 13° C. Plants were pinched and were two years old when the photographs and description were taken. In the following description, color references are made to The Royal Horticultural Society Colour Chart, 2015 Edition, except where general terms of ordinary dictionary significance are used.

Botanical classification: *Vaccinium corymbosum* 'FV1907'.

Parentage:

*Female, or seed, parent.*—*Vaccinium corymbosum* 'Emerald', disclosed in U.S. Plant Pat. No. 12,165.

*Male, or pollen, parent.*—*Vaccinium corymbosum* 'Snowchaser', disclosed in U.S. Plant Pat. No. 19,503.

Propagation:

*Type*.—By stem cuttings.

*Time to initiate roots, summer*.—About three weeks at temperatures about 26° C.

*Time to produce a rooted young plant, summer*.—About six weeks at temperatures about 26° C.

*Root description*.—Fine in thickness, fibrous, typically white to brown in color, actual color of the roots is dependent on substrate composition, water quality, fertilizer type and formulation, substrate temperature and physiological age of roots.

*Rooting habit*.—Shallow rooting; medium density.

Plant description:

*Plant and growth habit*.—Semi-upright and bushy plant habit; vigorous growth habit and moderate growth rate; plants produce fruit on one-year and current season's shoots.

*Plant height*.—About 104 cm.

*Plant diameter*.—About 52 cm.

Branch description:

*Quantity per plant*.—About five primary branches each with about 13 secondary branches each; pinching enhances branching potential.

*Length*.—About 60 cm to 70 cm.

*Diameter*.—About 8 mm.

*Internode length*.—About 2 cm to 2.5 cm.

*Strength*.—Strong.

*Aspect*.—Leaning outwardly.

*Texture and luster*.—Smooth, glabrous; matte.

*Color, developing and developed*.—Close to 144B; in the autumn, tinged with close to 176C to 176D; if woody, close to 199B.

Leaf description:

*Arrangement*.—Alternate; simple.

*Length*.—About 5.4 cm.

*Width*.—About 3.2 cm.

*Shape*.—Ovate.

*Apex*.—Acute.

*Base*.—Obtuse.

*Margin*.—Entire.

*Texture and luster, upper surface*.—Smooth, glabrous; semi- glossy.

*Texture and luster, lower surface*.—Smooth to rugose, glabrous; matte.

*Venation*.—Pinnate and reticulate.

*Color*.—Developing leaves, upper surface: Close to 137C. Developing leaves, lower surface: Close to 147C. Fully expanded leaves, upper surface: Close to 137B; in the autumn, tinged with close to 176C to 176D; venation, close to 144D. Fully expanded leaves, lower surface: Close to 147C; in the autumn, tinged with close to 176C to 176D; venation, close to 144D.

*Petioles*.—Length: About 4 mm. Diameter: About 2 mm. Strength: Moderately strong. Texture and luster, upper and lower surfaces: Smooth, glabrous; matte. Color, upper and lower surfaces: Close to 145A.

Flower description:

*Flower form and flowering habit*.—Single urceolate-shaped flowers arranged in panicles; freely flowering with about 50 to 70 flowers per inflorescence and about 500 to 800 flowers developing per plant during the flowering season; flowers, drooping and longitudinally ridged; flowers not persistent.

*Fragrance*.—None detected.

*Natural flowering season*.—In Lepe, Spain plants typically flower in November.

*Flower buds*.—Length: About 5 mm. Diameter: About 3 mm. Shape: Ovoid. Texture and luster: Smooth, glabrous; matte. Color: Close to 144B; anthocyanin development has not been observed.

*Inflorescence height*.—About 15 cm to 25 cm.

*Inflorescence diameter*.—About 5 cm to 10 cm.

*Flower diameter*.—About 1 cm.

*Flower depth* (*height*).—About 1 cm to 1.5 cm.

*Petals*.—Arrangement: Five petals, fused. Length: About 1 cm. Width: About 5 mm. Shape: Urceolate. Apex: Cuspidate. Margin, distal free part: Entire; moderately undulate. Texture and luster, upper and lower surfaces: Smooth, glabrous; matte. Color: When opening, upper surface: Close to NN155B tinged with close to 186D. When opening, lower surface: Close to NN155B. Fully opened, upper and lower surfaces: Close to NN155B; venation, close to NN155B; color becoming closer to 164A with development.

*Sepals*.—Arrangement: Five sepals, fused; erect to semi-erect and straight. Calyx length: About 5 mm. Calyx width: About 8 mm. Shape: Ovate. Apex: Acute. Margin: Entire. Texture and luster, upper and lower surfaces: Smooth, glabrous; matte. Color: When developing, upper and lower surfaces: Close to 143D. Fully opened, upper and lower surfaces: Close to 143D; in the autumn, tinged with close to 176C to 176D.

*Peduncles*.—Length: About 1 cm. Diameter: About 1 mm. Strength: Strong. Texture and luster: Smooth, glabrous; matte. Color: Close to 143D; in the autumn, tinged with close to 176C to 176D.

*Pedicels* (*flowers and fruits*).—Length: About 5 mm to 10 mm. Diameter: About 3 mm. Strength: Strong. Texture and luster: Smooth, glabrous; matte. Color: Close to 139C; in the autumn, tinged with close to 176C to 176D.

*Reproductive organs*.—Stamens: Quantity per flower: About ten. Filament length: About 4 mm. Filament color: Close to 164A. Anther size: About 2 mm by 2 mm. Anther color: Close to 164A. Pollen amount: Moderate. Pollen color: Close to 155D. Pistils: Quantity per flower: One. Pistil length: About 5 mm to 10 mm. Stigma diameter: About 1 mm. Stigma shape: Rounded. Stigma color: Close to 143C. Style length: About 8 mm. Style color: Close to 143C. Ovary color: Close to 143C.

*Fruits*.—Type: Berry. Quantity: One per flower; about 2.5 to 3 kilograms of fruits are formed on one-year old plants. Time to ripening: About one week. Keeping quality: Good postproduction longevity, about two weeks. Size: Large, about 2.5 cm. Weight: About 3.25 g. Shape: Roughly spherical. Firmness: Moderate. Texture and luster: Smooth, glabrous; matte. Flesh color: Close to 144D. Skin color, developing:

Close to 143C. Skin color: Close to 103A; bloom, close to NN155A. Taste: Very sweet; brix, close to 12.7%.

*Seeds*.—Quantity: About 10 to 20 per berry. Length: About 2 mm. Diameter: About 1 mm. Texture: Smooth, glabrous. Color: Close to 164A.

Pathogen & pest resistance: To date, plants of the new Blueberry have been observed to be resistant to pathogens and pests common to Blueberry plants.

Temperature tolerance: Plants of the new Blueberry have been observed to tolerate temperatures ranging from about 2° C. to about 40° C. and to be suitable for USDA Hardiness Zone 10.

It is claimed:

1. A new and distinct Blueberry plant named 'FV1907' as illustrated and described.

* * * * *